United States Patent [19]

Kauffman

[11] Patent Number: 5,071,527

[45] Date of Patent: Dec. 10, 1991

[54] COMPLETE OIL ANALYSIS TECHNIQUE

[75] Inventor: Robert E. Kauffman, Kettering, Ohio

[73] Assignee: University of Dayton, Dayton, Ohio

[21] Appl. No.: 545,842

[22] Filed: Jun. 29, 1990

[51] Int. Cl.$^5$ ............................................. G01N 27/26
[52] U.S. Cl. ................................ 204/153.1; 204/412; 204/434; 324/439; 436/60
[58] Field of Search ..................... 204/153.1, 412, 434; 324/439, 450

[56] References Cited

U.S. PATENT DOCUMENTS

| | | | |
|---|---|---|---|
| 4,132,605 | 1/1979 | Tench et al. | 204/153.1 |
| 4,146,437 | 3/1979 | O'Keefe | 204/153.1 |
| 4,317,705 | 3/1982 | Hamada et al. | 204/153.1 |
| 4,654,126 | 3/1987 | Amelio et al. | 204/153.1 |
| 4,701,713 | 10/1987 | Eaton et al. | 324/442 |
| 4,744,870 | 5/1988 | Kauffman | 436/60 |
| 4,764,258 | 8/1988 | Kauffman | 204/153.1 |
| 4,928,065 | 5/1990 | Lane et al. | 324/464 |

*Primary Examiner*—T. Tung
*Attorney, Agent, or Firm*—Killworth, Gottman, Hagan & Schaeff

[57] ABSTRACT

A method and apparatus is disclosed for the complete analysis of used oils, lubricants, and fluids. The method can monitor antioxidant depletion, oxidation initiators buildup, product buildup, or liquid contamination or combinations thereof. The method can be performed either on-line or off-line but is preferably an on-line system, either a built-in system or a dip-stick type system, having a working microelectrode, a reference electrode, and an auxiliary electrode. A sample is contacted by the electrodes and subjected to cyclic voltammetric analysis, whereby a varying electric current is produced within the sample. The current is measured and recorded, and the conductance is measured. The remaining useful life of the oil, lubricant, or fluid is then determined from the wave heights of the oxidation and reduction peaks, and the contamination is determined from the conductance.

19 Claims, 5 Drawing Sheets

COMPLETE OIL ANALYSIS TECHNIQUE

The United States government has rights in this invention, pursuant to Contract No. F 33615-88-C-2817 awarded by the Department of the Air Force.

BACKGROUND OF THE INVENTION

The present invention relates generally to a method and apparatus for evaluating oils, lubricants, and fluids, and, more specifically, to a method and apparatus for complete analysis, including on-line analysis, of used oils, lubricants, and fluids.

Oils, lubricants and other fluids are often used in ways that cause their degradation. For example, it is common to lubricate and cool the components of operating equipment by wetting them with an oil or lubricant. As it carries out these functions, the oil or lubricant experiences various environmental stresses that cause its basestock to undergo thermal-oxidative degradation.

Oils are also used as transmission fluids and are used in hydraulic systems. In these cases, the oil is subjected to pressures, frequent movement, and heat. These stresses also degrade the oil.

Cooking oils are another type of oils that undergo severe thermal-oxidative stresses. The degradation of the basestock can lead to the production of acids within the oil which affect the taste of the food.

Because of this degradation, antioxidants are frequently added to oils, lubricants, or fluids to protect their characteristics. As long as the antioxidant system remains intact, the oxidative degradation of the basestock is minimal, and so are changes in the properties.

The antioxidants in the oil, lubricant, or fluid are gradually depleted over time. Eventually, the antioxidants become ineffective, allowing large changes in the physical properties of the basestock to occur. At that point, the oil, lubricant, or fluid is no longer able to protect the equipment, and its useful life is over. The use of oil, lubricant, or fluid in this condition can result in excessive component wear and eventual equipment failure.

Not all oils, lubricants, and fluids contain antioxidants. In that case, the degradation of the basestock can lead to the production of acids within the oil, lubricant or fluid which render it useless. Cooking oils, for example, become rancid.

Since it is undesirable to use, for example, a lubricant beyond the end of its useful life, scheduled lubricant changes have been established for various types of equipment. The length of operating time between scheduled changes is chosen very conservatively so that lubricant which is beyond its useful life does not remain in the equipment. However, this approach results in discarding lubricants which still have useful life.

Another problem facing users of oils, lubricants, and other fluids is liquid contamination. If coolant from another part of the system leaks into the lubrication system, for instance, the lubricant could become useless for that reason.

The ability to analyze oils, lubricants, and other fluids for antioxidant depletion, oxidation initiator, product buildup, and liquid contamination would eliminate the need to perform oil, lubricant, or fluid changes on the basis of a fixed schedule. This would allow longer use of oil, lubricant, or fluid, providing savings in material and labor costs. In addition, abnormal depletion rates for antioxidants may indicate accelerated oil oxidation leading to severe wear problems prior to equipment failure. Early detection of liquid contamination is also important, as is early detection of failures in cooking oils.

Various thermal-oxidative and chemical-oxidative stressing techniques which permit evaluation of remaining useful life of the oil, lubricant, or fluid are known. However, most of these techniques are unsuitable for routine use. Thermal-oxidative stressing techniques require the use of high temperatures and pressures and relatively long analysis times, about 30 minutes. Chemical-oxidative stressing techniques are difficult in operation, require unstable reagents, and require even longer analysis times, up to two hours.

U.S. Pat. Nos. 4,744,870 and 4,764,258 to Kauffman and assigned to the same assignee as the present invention disclose methods for determining the remaining useful life of oils which are fast, very accurate, easy to operate, and which can be performed with inexpensive equipment. In these methods, lubricant samples are mixed with a solvent, an electrolyte, and either an organic base or a solid substrate, depending on the type of oil to be tested. The sample is placed in an electrolytic cell and subjected to a cyclic voltammetric analysis. The current generated during the cyclic voltammetric analysis is measured and recorded. The remaining useful life for the lubricant is then determined from the oxidation or reduction wave height. However, these methods can only be performed off-line and are limited to oils or lubricants containing antioxidants.

Therefore, there remains a need for a method and apparatus which can be used on-line to test antioxidant depletion, oxidation initiator buildup, product buildup, or liquid contamination of used oils, lubricants, and other fluids.

SUMMARY OF THE INVENTION

The present invention solves this need by providing a method and apparatus for complete analysis of oils, lubricants, and fluids, which method and apparatus can be used on-line; although, the unique complete analysis method of the present invention can also be used off-line if so desired. In any event, the complete analysis system of the present invention can monitor the antioxidant depletion, oxidation initiator, product buildup, or liquid contamination of used oils, lubricants, and fluids.

The method includes applying an electrical potential of a first value to the electrode to produce an electrical current through a sample of the used oil, lubricant, or fluid either off-line with an extracted sample or on-line with a continuously changing sample or with a sample in an on-line sample reservoir. The potential is varied cyclically from the first value to a second value, producing an oxidation reaction of the antioxidant species, and then back to the first value, producing a reduction reaction of the oxidized product. The potential is then varied from the first value to a third value, producing a reduction reaction of the peroxide and other oxidized species, and then back to the first value, producing an oxidation reaction of the reduced product. Current produced in the cell is measured and recorded. These steps of cyclically varying potential and recording measured current essentially constitute a cyclic voltammetric evaluation of the oil, lubricant, or fluid.

The conductivity of the oil, lubricant, or fluid is also measured using the electrodes. The heights of the oxidation and reduction waves and the conductivity measurement are then used to determine the remaining useful life and the contamination of the used oil, lubricant, or fluid.

The on-line system involves monitoring for antioxidant depletion, oxidation initiator buildup, product buildup, or liquid contamination, or combinations thereof. By simultaneously monitoring for two or more of these conditions as is preferred, significant advantages are obtained. In lubrication systems, the analytical results can be used to predict the length of equipment operating time before the oil or lubricant becomes dysfunctional eliminating the need for scheduled oil or lubricant changes. The present method can also be used to detect abnormal operating conditions which accelerate oil or lubricant degradation prior to severe wear and equipment failure in lubrication systems, spoilage of the oil or fluid in cooking systems, etc. For example, in the case of aircraft turbine engines, the capability of the present method to detect engines experiencing severe oil degradation can possibly even provide the additional benefit of saving lives.

The on-line analysis can involve either a built-in electrode system or a dip-stick type electrode system. In the built-in system, electrodes (preferably a working microelectrode, a reference electrode, and an auxiliary electrode) are permanently attached to a source (such as a return line) of an essentially continuously changing sample of used oil, lubricant or fluid or to a use container for the oil, lubricant or fluid (such as a deep fryer). The current measurement and recording in this instance can be intermittent at various intervals or continuous. In the dip-stick type system, electrodes (preferably a working microelectrode, a reference electrode, and an auxiliary electrode) with an attached temperature probe or heating element are placed in an on-line sample reservoir (such as an oil pan, deep fryer or portions of such reservoirs) for the used oil, lubricant or fluid. The electrodes and temperature probe or heating element are in this instance preferably removed when the analysis is concluded.

The off-line analysis preferably involves simultaneous analysis for antioxidant depletion and oxidation initiator level; although, it may involve analysis for antioxidant depletion, oxidation initiator buildup, product buildup, or liquid contamination or combinations thereof. An extracted portion of the used oil, lubricant or fluid is diluted with a solvent, preferably a nonpolar solvent, to produce a sample to be analyzed. Electrodes are placed in that sample and the analysis is conducted in the same manner as in the on-line method.

Accordingly, it is an object of the present invention to provide a complete method of analyzing used oils, lubricants, and fluids which is fast, easy to perform, and which can be used either on-line or off-line. It is another object of the invention to provide a method which permits monitoring of antioxidant depletion, oxidation initiator buildup, product buildup, or liquid contamination or combinations thereof. It is another object of the invention to provide an on-line system for analyzing used oils, lubricants, and fluids. Other objects and advantages of the present invention will be apparent from the following description, the accompanying drawings, and the claims.

DETAILED DESCRIPTION OF THE PREFERRED EMBODIMENTS

The method for analyzing used oil, lubricant, or fluid in accordance with the present invention is based upon cyclic voltammetric analysis of a sample of the used oil, lubricant, or fluid and on conductivity measurements. In general, voltammetric techniques are electroanalytical methods wherein electrodes are placed in the sample to be tested. Data is obtained by measuring the current passing through the sample as a function of the potential applied, and test results are based on current, voltage, and time relationships at the cell electrodes.

Figure 1:
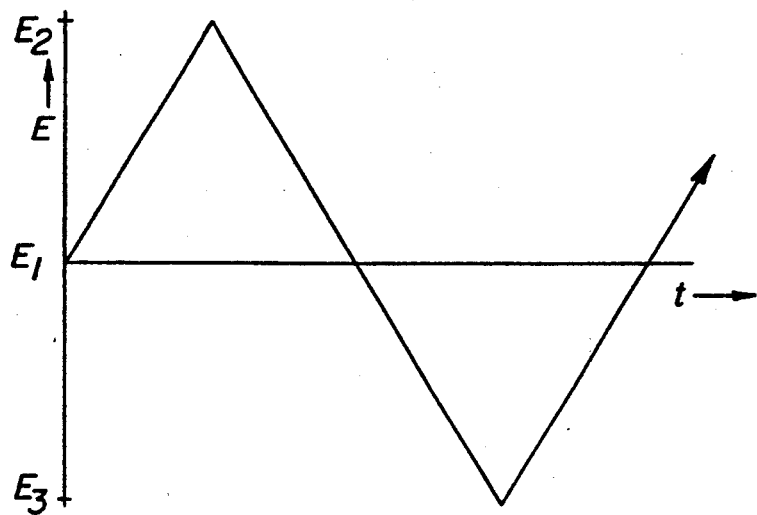
FIG. 1 is a plot illustrating potential applied to an oil, lubricant, or fluid sample as a function of time in practicing the method for evaluating used oil, lubricant, or fluid in accordance with the present invention.

In performing a voltammetric analysis, the potential across the electrodes is varied linearly with time, and the resulting current is recorded as a function of the potential. A variation of this technique, known as cyclic voltammetric analysis, uses a potential variation as shown in FIG. 1. Initially, potential applied to the electrodes is of a first value $E1$ and is linearly increased over time to the second value $E2$. The potential is next reduced at the same rate until the potential again returns to $E1$. The potential continues to be reduced until it reaches a third value $E3$. The potential is then increased until it returns to $E1$, producing a sawtooth waveform. The cycle may then be repeated.

The present invention is based in part upon subjecting a sample of the used oil, lubricant, or fluid to cyclic voltammetric analysis. As the increasing voltage is applied to the sample, the antioxidant species within the used oil, lubricant, or fluid are caused to electrochemically oxidize. During voltage reduction, the oxidized species are subsequently electrochemically reduced. The voltage is then reduced until the peroxide and other oxidized species within the oil, lubricant, or fluid are caused to electrochemically reduce. When the voltage is increased, these reduced species are electrochemically oxidized. The data recorded during these oxidation and reduction reactions can then be used to determine the remaining useful life of the oil, lubricant, or fluid.

Figure 2:
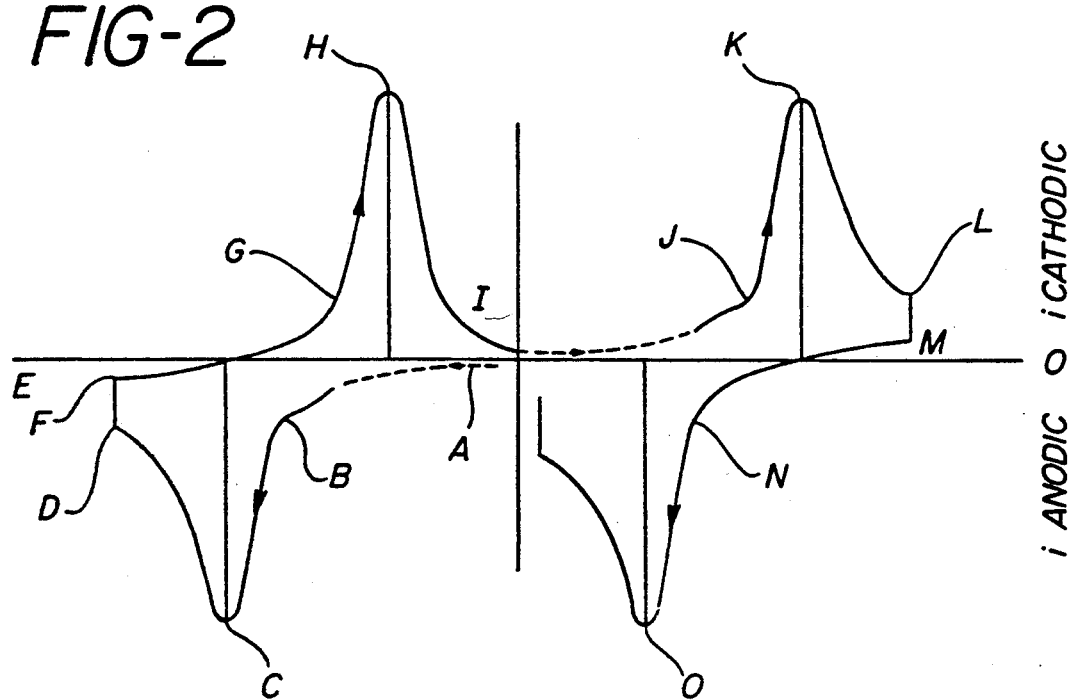
FIG. 2 is a plot illustrating current produced in the sample as a function of potential applied.

A typical current-potential curve produced during the practice of the present invention can be seen by reference to FIG. 2. Initially, as shown at point A, the applied potential produces an electrochemical reaction having a rate so slow that virtually no current flows. As the voltage increases, shown at point B, the antioxidant species in the sample begin to oxidize at the electrode's surface, producing an anodic rise in the current. As the potential is further increased, the decrease in the electro-active species concentration at the electrode surface and the exponential increase of the oxidation rate lead to a maximum in the current-potential curve shown at point C. The current then decreases to the diffusion-limited anodic current value at point D. The peak so produced is referred to as the oxidation wave.

The direction of the applied voltage is then reversed, point F, and becomes more cathodic with time. When the voltage becomes sufficiently cathodic, the oxidized species at the surface of the electrode begin to reduce, producing the cathodic rise in the current shown at point G. Again, a maximum current is obtained at point H, and the current decreases with decreasing potential until the positive voltage half cycle is completed shown at point I. This produced peak is referred to as the reduction wave.

As the voltage changes from positive to negative, the applied potential produces a reaction with a rate so slow that almost no current flows. As the voltage becomes more negative, shown at point J, the peroxide and other oxidized species in the sample begin to reduce at the surface of the electrode, producing a cathodic rise in the current. A maximum current is obtained at point K, and then the current begins to decrease to the diffusion limited cathodic current at point L is reached. This peak is a reduction wave.

The direction of the applied voltage is then reversed, point M, and becomes more anodic with time. When it becomes sufficiently anodic, the reduced species at the surface of the electrode begin to oxidize, producing the anodic rise in the current shown at point N. A maximum current is obtained at point O, and the current decreases until the negative voltage half cycle is completed or a new cycle is initiated. This peak is an oxidation wave.

The conductance of the sample is then measured using the electrodes. The conductivity measurements are used primarily to detect leaks in coolant systems. If there is a coolant leak, highly polar liquids will come into contact with the lubrication system. This will cause a rapid increase in the conductivity of the oil.

Once the voltammetric analysis and conductance measurements have been performed, the results are analyzed. Either the maximum peak height or the area under the peak is compared to data previously taken. When the antioxidant level falls below a preselected value, or the level of peroxide and other oxidized species exceeds a preset value, or the change in either one exceeds a preset value, then the oil, lubricant, or fluid has reached the end of its useful life. In a similar fashion, the conductivity values are compared to previous data and to certain preselected values. The exact levels chosen depend upon the type of oil, lubricant, or fluid, the type of antioxidant, oil consumption rates, and other factors. These values can be determined through testing of the specific system being used.

Figure 3:
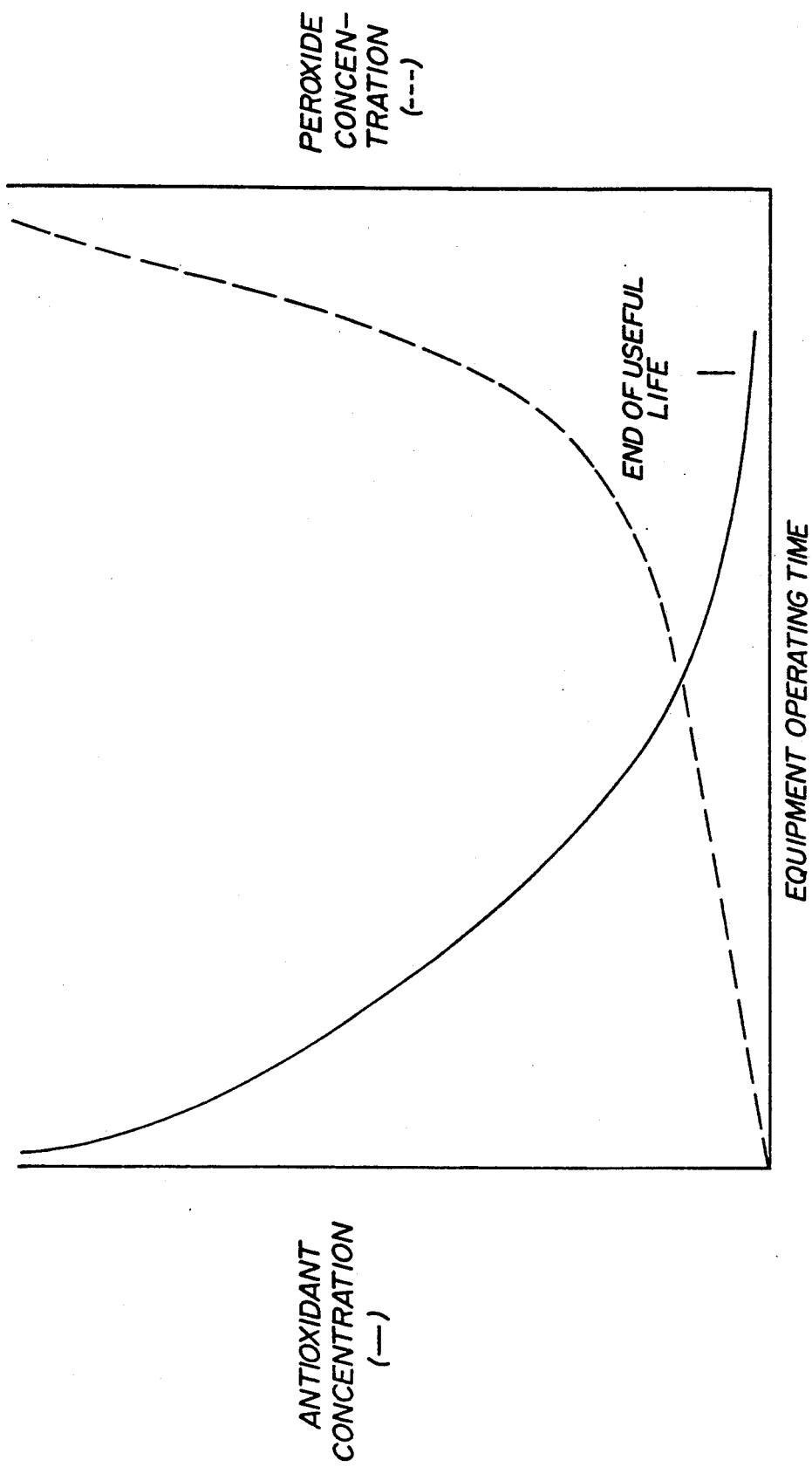
FIG. 3 is a plot indicating typical results produced by the evaluation method for antioxidant depletion and oxidation initiator levels.

FIG. 3 shows typical results obtained with the oil evaluation technique for antioxidant depletion and oxidation initiator (peroxide) levels. At some point, the antioxidant level becomes so low that it no longer operates to protect the oil, lubricant, or fluid's properties. In non-inhibited oils, lubricants, and fluids, i.e. those without antioxidants, the level of peroxide and other oxidized species may increase to a point that the oil, lubricant, or fluid cannot be used any longer.

Figure 4:
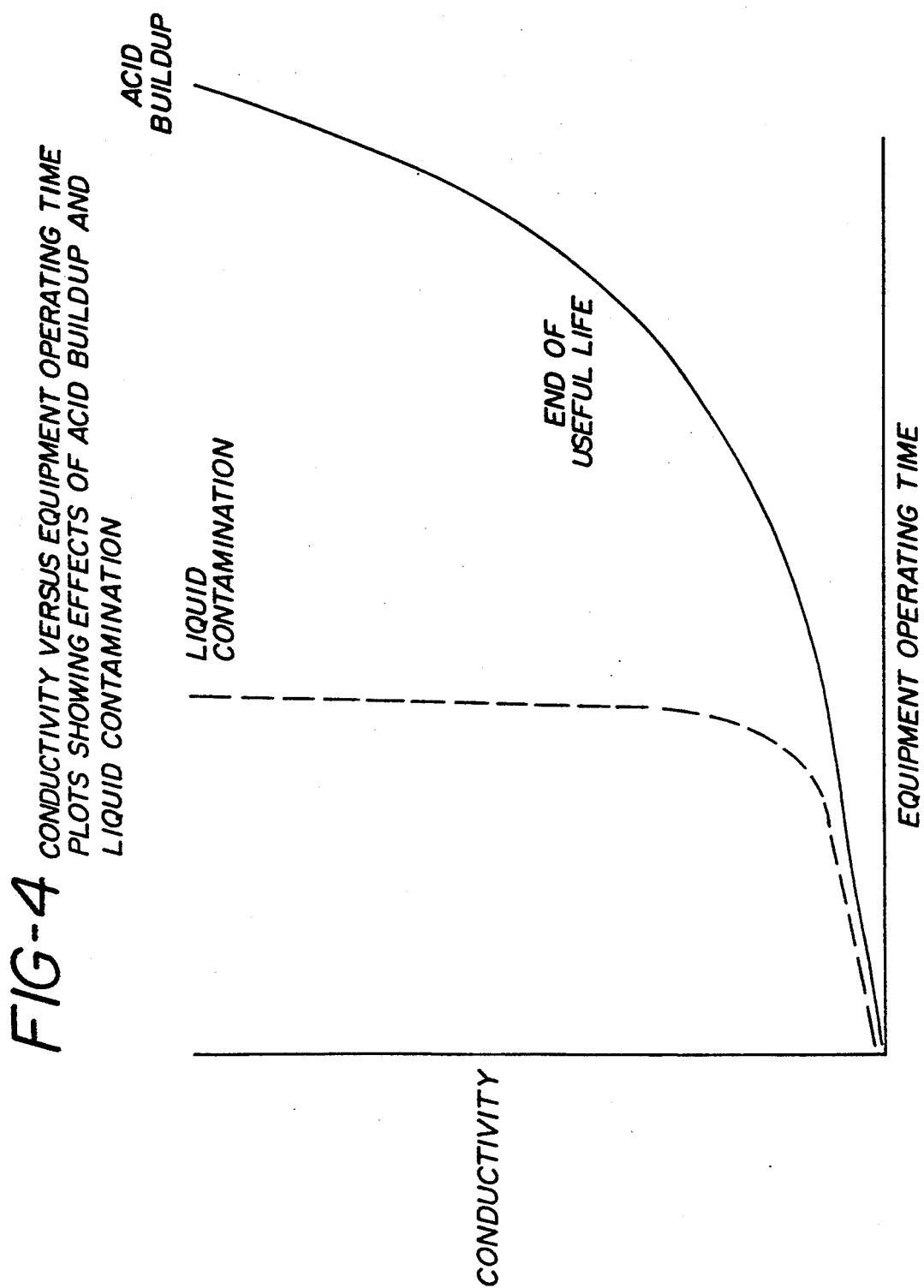
FIG. 4 is a plot indicating typical results produced by the evaluation method for conductance showing a simulation of liquid contamination.

Another problem may be coolant leakage into the oil, lubricant or fluid. FIG. 4 shows a simulated plot of a coolant leak. The conductivity rises much faster than would usually be the case, indicating a leak.

The voltage scan rate can be any rate, but is preferably 1 V/sec. The varying of the potential from the first value to the second value back to the first value and to the third value and back to the first value may be done from one half cycle to 10 cycles, with one cycle preferred.

In carrying out the cyclic voltammetric analysis, the potential is varied between $+120$ V and $-120$ V, variation between $+30$ V and $-30$ V being preferred. This voltage range is much larger than that used in any prior U.S. Pat. Nos. 4,744,870 and 4,764,258 and the working electrode is much smaller.

The result is that in addition to antioxidant depletion, the present system may also be used to perform peroxide (oxidation initiators), carboxylic acid (oxidation products), and water contamination (coolant leak) determinations or combinations thereof. Such a complete analysis is not possible with the system of the earlier Kauffman patents.

Even more significantly, the present system has on-line capabilities which are not found in the system of the earlier Kauffman patents. On-line capabilities are extremely important in that it makes use of an extracted sample unnecessary.

The on-line analysis can involve either a built-in electrode system or a dip-stick type electrode system. The built-in system has the advantage of analyzing the used oil, lubricant, or fluid in use or on its return before it is diluted in a reservoir. Therefore, it is more sensitive to abnormal operating conditions than the dip-stick electrode system, which monitors the diluted oil, lubricant, or fluid in the reservoir, which may be considered a sample reservoir. With the built-in electrode, the condition of the oil, lubricant, or fluid can be monitored intermittently at various intervals or continuously. The dip-stick electrode does not require any equipment modification prior to use, however. In addition, it can be cleaned and checked between uses to eliminate the effects of electrode filming, erosion, or other problems which may have an effect on the long term accuracy of the built-in electrode. A temperature probe or heating element should be incorporated into the dip-stick electrode to improve the accuracy of this system since the sample temperature will depend on the time between equipment stoppage and analysis.

Figure 5:
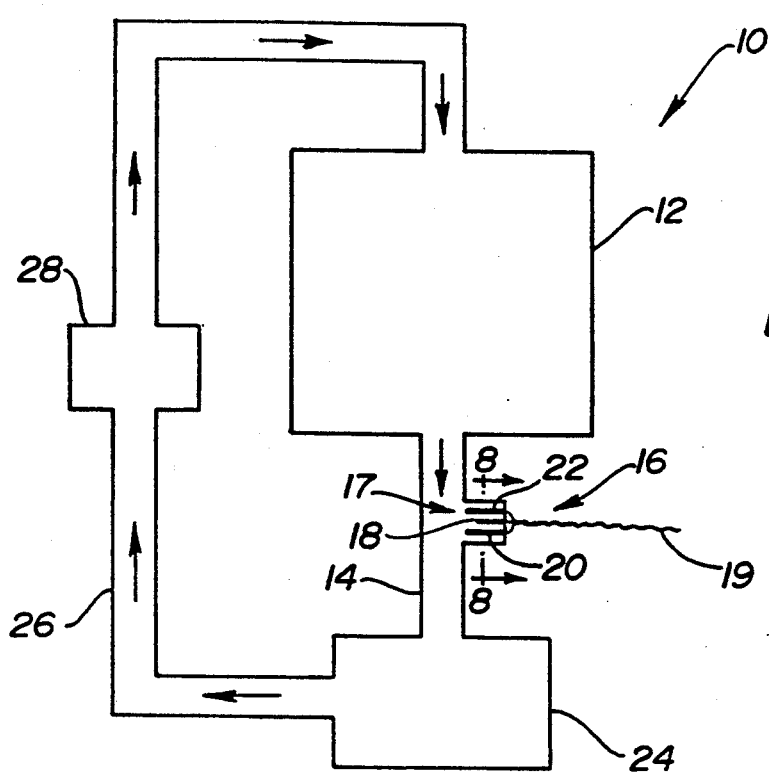
FIG. 5 is a schematic view of an on-line system involving an essentially continuously changing sample.

Referring to FIG. 5 there is shown in schematic form a built-in on-line system 10. System 10 includes a piece of equipment 12 through which oil, lubricant or fluid passes. The used oil, lubricant or fluid flows through return line 14 into reservoir 24 from whence it may be recirculated through line 26 by oil pump 28. In return line 14 there is found permanently attached thereto analyzer 16 in chamber 17. Analyzer 16 preferably comprises a working microelectrode 18, a reference electrode 20 and an auxiliary electrode 22, and lead(s) 19.

Figure 6:
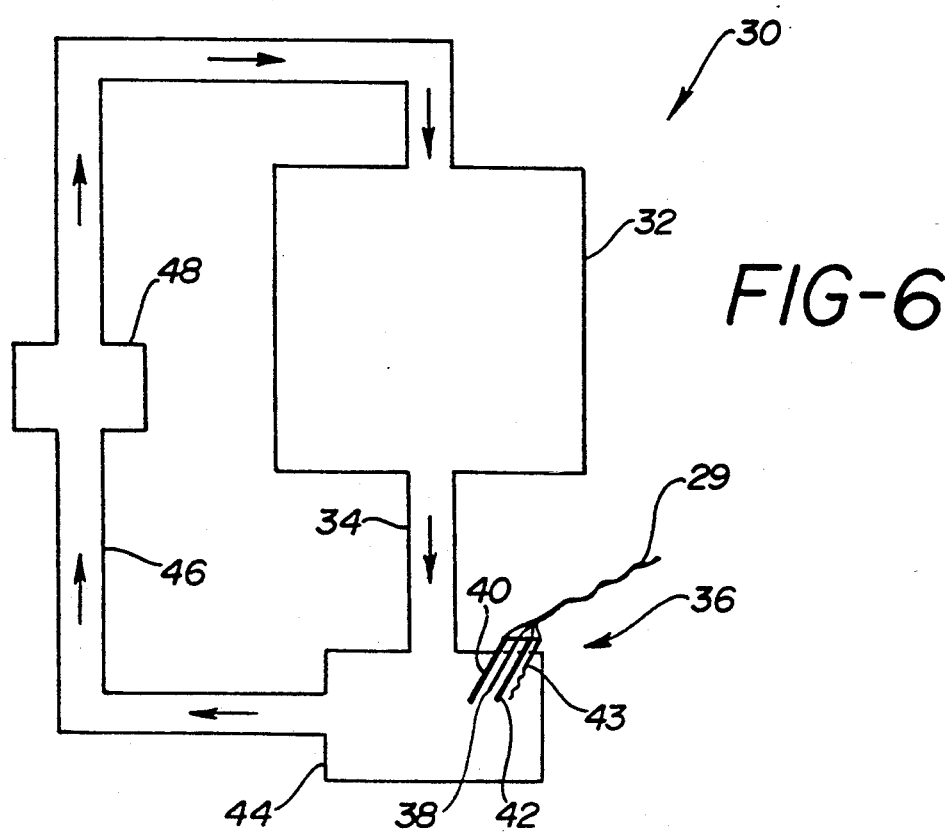
FIG. 6 is a schematic view of an on-line system involving a sample reservoir.

Referring to FIG. 6 there is shown in schematic form a dip-stick type on-line system 30. System 30 includes a piece of equipment 32 through which oil, lubricant or fluid passes. The used oil, lubricant or fluid flows through return line 34 into on-line sample reservoir 44 from whence it may be recirculated through line 46 by oil pump 48. Analyzer 36 comprising a working microelectrode 38, a reference electrode 40, and auxiliary electrode 42, and a temperature probe or heating element 43 is placed through an appropriate opening into reservoir 44 for the analysis, connected to lead(s) 29. Analyzer 36 may be removed after the analysis is completed and replaced by a normal dip-stick or the opening capped.

Figure 7:
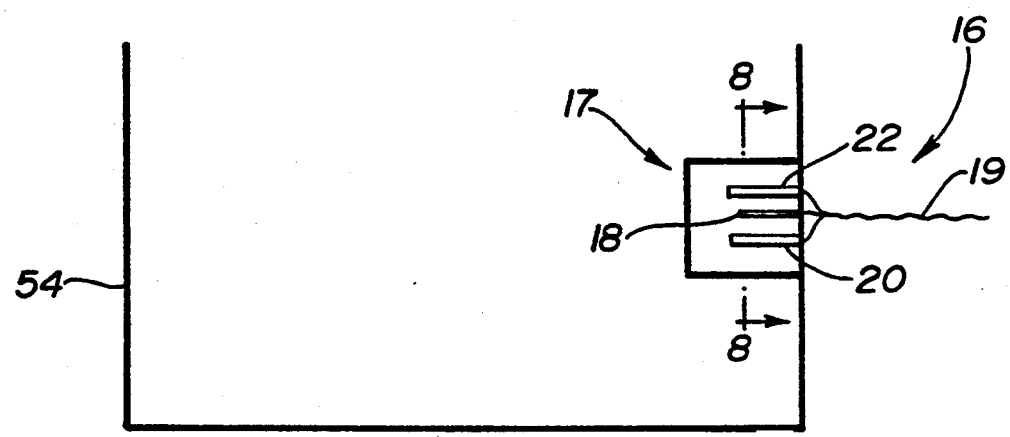
FIG. 7 is a schematic view of an on-line system involving a use container.
Figure 8:
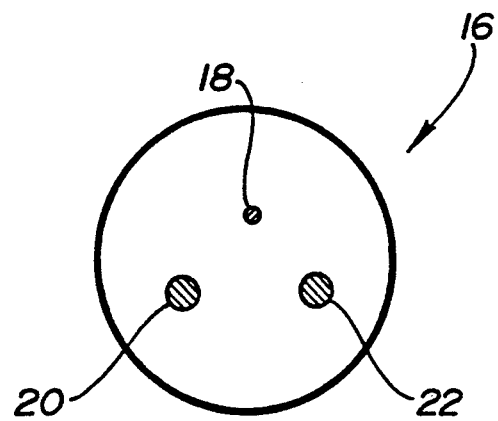
FIG. 8 is a cross-sectional view along line 8—8 of FIGS. 5 and 7.

FIG. 7 shows in schematic form a built-in system similar to FIG. 5, where like numerals are used, except that the sample need not be essentially continuously changing, nor need there be a return line. Rather an analyzer 16 may be placed in a chamber 17 on the side of a use container 54 (such as a deep fryer or gear box) connected to lead(s) 19. FIG. 8, then, shows a cross-sectional view of analyzer 16, with a working microelectrode 18, a reference electrode 20 and an auxiliary electrode 22. Since a use container 54 is involved, the use temperature should be known. Many deep fryers, for example, have temperature controls and/or temperature probes from which this can be fairly accurately determined. A temperature probe or heating element would not be added in this system unless necessary.

In all of the systems illustrated by FIGS. 5–8, the working, reference, and auxiliary electrodes may be made from any material which is conductive. Platinum and gold are the preferred materials.

The working electrode should have a surface area of less than 0.3 mm$^2$, preferably $8 \times 10^{-5}$ mm$^2$. The reference and auxiliary electrodes may be of similar size and may have surface areas smaller or greater than the surface area of the working electrode. Preferably both have a surface area of 0.2 mm$^2$.

The temperature of the sample for the on-line method can vary between 20° and 400° C. It is dependent on the temperature of the operating equipment unless a heating element is included, in which case an analysis at a set temperature can be assured. In any event the temperature of the sample should be known from the various factors discussed above with regard to each system.

To perform this method off-line, a portion of the used oil, lubricant, or fluid is extracted and diluted with a solvent, preferably a nonpolar solvent, to produce a sample. The electrodes are then placed in the sample and the cyclic voltammetric analysis is performed. No electrolyte need be added. The results are analyzed in the same way as for the on-line method.

When this method is used off-line, antioxidant depletion and oxidation initiator levels are preferrably measured. It is harder to measure the liquid contamination and oxidation product buildup because the used oil, lubricant, or fluid is diluted with a solvent; although, in some instances this may also be done. While a nonpolar solvent is preferred, any solvent which is capable of dissolving the used oil, lubricant, or fluid, can be used. The solvent to oil, lubricant, or fluid ratio by volume in the sample should be between 1:1 and 1:500, preferably 1:10.

While the off-line method can be used for determining the remaining useful life of an oil, lubricant, or fluid, it is a less accurate method for this determination than that disclosed in the two Kauffman patents mentioned in the Background of the Invention. Once the on-line method has indicated that the oil, lubricant, or fluid is degraded or there is an abnormal operating condition, the method of the Kauffman patents can be used to determine the exact remaining useful life of the used oil, lubricant, or fluid (assuming one of these methods can be used).

It may not be desirable to monitor the antioxidant species on-line with this method because the antioxidant species are oxidized, accelerating their depletion and decreasing the remaining life of the oil, lubricant, or fluid; although, this is not a major problem since such minor amounts are involved. Besides, the electrochemical reduction of the peroxide and other oxidized species should extend the life of the oil, lubricant, or fluid by depleting the peroxides which accelerate thermal oxidation balancing out any decrease in life from the antioxidant depletion measurement. Accordingly, the on-line system may be used for monitoring antioxidant depletion, oxidation initiator buildup, product buildup, or liquid contamination or combinations thereof.

The present invention can be used to monitor oils, lubricants, and fluids in many different applications, for example, gas turbine engines, combustion engines, transmission systems, hydraulic systems, gear boxes, operating machinery, and deep fryers such as those frequently used in restaurants. Other uses will be apparent to those skilled in the art.

While the method herein described constitutes a preferred embodiment of this invention, it is to be understood that the invention is not limited to this precise method and apparatus, and that changes may be made therein without departing from the scope of the invention, which is defined in the appended claims.

What is claimed is:

1. A method for analyzing oil for antioxidant depletion, oxidation initiator buildup, product buildup, or liquid contamination, or combinations thereof, comprising the steps of:
    bringing electrodes into contact with a sample of oil;
    applying an electric potential of a first value to the sample to produce an electric current therethrough;
    varying the potential from the first value to a second value to produce an oxidation reaction;
    varying the potential from the second value to the first value to produce a reduction reaction;
    varying the potential from the first value to a third value to produce a reduction reaction;
    varying the potential from the third value to the first value to produce an oxidation reaction;
    measuring and recording the current during the oxidation and reduction reactions; and
    measuring the conductance of the oil.

2. The method of claim 1 wherein said electrodes include a working microelectrode, a reference electrode and an auxiliary electrode.

3. The method of claim 1 wherein two or more of antioxidant depletion, oxidation initiator buildup, product buildup or liquid contamination are simultaneously monitored.

4. The method of claim 1, wherein the first, second, and third potential values are within the range of +120 V and −120 V.

5. The method of claim 4, wherein the first, second and third potential values are +30 V, 0 V, and −30 V, respectively.

6. The method of claim 5 wherein the potential is varied at the rate of 1 V/sec.

7. The method of claim 1, wherein the step of bringing electrodes into contact with the sample includes attaching the electrodes on-line.

8. The method of claim 7, wherein the step of measuring and recording the current is done continuously.

9. The method of claim 7, wherein the step of measuring and recording the current is done intermittently.

10. The method of claim 1, wherein the step of bringing electrodes into contact with the sample includes placing the electrodes in an on-line sample reservoir, and then removing the electrodes from the sample reservoir when the analysis is concluded.

11. The method of claim 10, comprising the further step of attaching a temperature probe or heating element to the electrodes.

12. The method of claim 1 wherein the step of bringing electrodes into contact with the sample includes extracting a portion of the oil from the system, mixing with a solvent to produce a sample to be analyzed, and placing the sample into an off-line electrolytic cell.

13. The method of claim 12 wherein the solvent is a nonpolar solvent.

14. An on-line method for analyzing oil for antioxidant depletion, oxidation initiator buildup, product buildup, or liquid contamination, or combinations thereof, comprising the steps of:
attaching electrodes to a source of a sample of oil,
applying an electric potential of a first value to the sample to produce an electric current therethrough;
varying the potential from the first value to a second value to produce an oxidation reaction;
varying the potential from the second value to the first value to produce a reduction reaction;
varying the potential from the first value to a third value to produce a reduction reaction;
varying the potential from the third value to the first value to produce an oxidation reaction;
measuring and recording the current during the oxidation and reduction reactions; and
measuring the conductance of the oil.

15. The method of claim 14 wherein said electrodes include a working microelectrode, a reference electrode and an auxiliary electrode.

16. The method of claim 15 wherein said electrodes are placed in a chamber attached to a use container for said oil.

17. The method of claim 15 wherein said electrodes are placed in a chamber attached to a return line for said oil.

18. An on-line method for analyzing oil for oxidation initiator buildup, product buildup, and liquid contamination, comprising the steps of:
placing electrodes with a temperature probe or heating element attached thereto in an on-line sample reservoir,
applying an electrical potential of a first value to a sample in said on-line sample reservoir to produce an electric current therethrough;
varying the potential from first value to a second value to produce an oxidation reaction;
varying the potential from the second value to the first value to produce a reduction reaction;
varying the potential from the first value to a third value to produce a reduction reaction;
varying the potential from the third value to the first value to produce an oxidation reaction;
measuring and recording the current during the oxidation and reduction reactions;
measuring the conductance of the oil and
removing the electrodes and temperature probe or heating element from said on-line sample reservoir when the analysis is concluded.

19. The method of claim 18 wherein said electrodes include a working microelectrode, a reference electrode and an auxiliary electrode.

* * * * *